(12) United States Patent
Hu et al.

(10) Patent No.: US 11,054,405 B2
(45) Date of Patent: Jul. 6, 2021

(54) TESTING DEVICE AND METHOD FOR SIMULATING THE FLOWBACK IN THE SHUT-IN PERIOD OF FRACTURED WELLS

(71) Applicant: SOUTHWEST PETROLEUM UNIVERSITY, Chengdu (CN)

(72) Inventors: Yongquan Hu, Chengdu (CN); Chaoneng Zhao, Chengdu (CN); Jinzhou Zhao, Chengdu (CN); Pengju Song, Chengdu (CN); Qiang Wang, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 0 days.

(21) Appl. No.: 16/923,078

(22) Filed: Jul. 7, 2020

(65) Prior Publication Data

US 2020/0333314 A1    Oct. 22, 2020

(30) Foreign Application Priority Data

Jul. 8, 2019 (CN) .......................... 201910609395.8

(51) Int. Cl.
   *E21B 49/02*     (2006.01)
   *G01N 3/10*      (2006.01)
   (Continued)

(52) U.S. Cl.
   CPC ............. *G01N 33/24* (2013.01); *E21B 49/02* (2013.01); *G01N 3/10* (2013.01); *G01N 29/06* (2013.01);
   (Continued)

(58) Field of Classification Search
   CPC ......... E21B 49/02; E21B 43/26; G01N 29/06; G01N 3/10; G01N 33/24; G01N 2291/102;
   (Continued)

(56) References Cited

U.S. PATENT DOCUMENTS 10,794,867 B2 * 10/2020 Chung ................. G01N 29/223
10,941,642 B2 *  3/2021 Gu ........................ E21B 43/267
   (Continued)

FOREIGN PATENT DOCUMENTS

CN       105114049     * 12/2015
CN        08166963     *  6/2018
   (Continued)

*Primary Examiner* — Jacques M Saint Surin (57) ABSTRACT

The invention discloses a testing device and method for simulating the flowback in the shut-in period of fractured wells, comprising a fracturing fluid tank, a flowback fracturing fluid tank, a hydraulic fracturing pump, a flowback fluid collection beaker, and a shut-in flowback testing system; the shut-in flowback testing system is composed of a box body and an acoustic wave testing device, a temperature control device, a fracturing string and a square rock block arranged in the box body; a stress loading plate and a hydraulic block are successively arranged between the four surfaces of the square rock block and the inner walls of the box body; the acoustic wave testing device consists of an acoustic wave transmitting probe and an acoustic wave receiving probe; the four outer surfaces of the box body are provided with hydraulic tanks.

2 Claims, 8 Drawing Sheets

(51) Int. Cl.
*G01N 29/06* (2006.01)
*G01N 33/24* (2006.01)
*E21B 43/26* (2006.01)

(52) U.S. Cl.
CPC ...... *E21B 43/26* (2013.01); *G01N 2203/0067* (2013.01); *G01N 2291/0232* (2013.01); *G01N 2291/0289* (2013.01); *G01N 2291/048* (2013.01); *G01N 2291/102* (2013.01)

(58) Field of Classification Search
CPC ... G01N 2291/0289; G01N 2291/0232; G01N 2203/0067; G01N 2291/048
USPC .......................................................... 702/2
See application file for complete search history.

(56) References Cited

U.S. PATENT DOCUMENTS

2008/0257545 A1* 10/2008 Abass ................... E21B 43/267
    166/250.01
2016/0202216 A1* 7/2016 Komiya ................. G01N 29/07
    73/598
2018/0171769 A1* 6/2018 Gu ........................ E21B 49/008
2019/0338621 A1* 11/2019 Jin ........................ E21B 47/107
2020/0225137 A1* 7/2020 Manning .................. G01N 3/08
2020/0386659 A1* 12/2020 Li .......................... E21B 44/04

FOREIGN PATENT DOCUMENTS

CN         109490507 A      3/2019
WO     WO2018006585    *  1/2018

* cited by examiner

TESTING DEVICE AND METHOD FOR SIMULATING THE FLOWBACK IN THE SHUT-IN PERIOD OF FRACTURED WELLS

TECHNICAL FIELD

The present invention relates to a testing device and method for simulating the flowback in the shut-in period of fractured wells, belonging to the technical field of hydraulic fracturing.

DESCRIPTION OF PRIOR ART

In recent years, the effective development of unconventional oil and gas reservoirs has become a hot topic in the global oil and gas development. In the commercial development of the shale gas, large amounts of slick water and proppant should be pumped with large displacements to maintain the opening and extension of fracturing fractures and realize the purpose of breaking the reservoir, thus forming a complex fracture network system. After the fracturing is completed, it is usually necessary to conduct flowback operation of about 10 days to discharge the residual fracturing fluid in the fractures, reducing the plugging effect of the fracturing fluid remaining in the fractures and its damage to the reservoir. It is generally considered that a higher flowback rate is better. Whereas, in recent years, researchers have found that the flowback rate is extremely low in most unconventional fracturing reservoirs. Studies show that (Vandecasteele, I., et al., Impact of Shale Gas Development on Water Resources: A Case Study in Northern Poland. Environmental Management, 2015. 55(6): p. 1285-1299.; Yan Q, Lemanski C, Karpyn Z T, Ayala L F. 2015. Experimental investigation of shale gas production impairment due to fracturing fluid migration during shut-in time [J]. Journal of Natural Gas Science and Engineering, 24: 99-105.), in the development of the shale gas throughout the United States, the average amount of the fracturing fluid flowing back from the reservoir is only 6% to 10% of the injected amount, indicating that most of the fracturing fluid is still trapped in the reservoir and seeps into the shale through various paths such as shale matrix, micro-fracture or fracture network structure. The relevant data shows that the flowback rate is 20% in Barnett and Eagle Ford shale fields, only 5% in Haynesville shale gas field (Nicot, J. and B. R. Scanlon, Water Use for Shale-Gas Production in Texas, U.S. Environmental Science & Technology, 2012. 46(6): p. 3580-3586.), and 5 to 10% in Fuling shale gas field in China (Zou Cai, Dong Dazhong, Wang Yuman, et al. Shale Gas in China: Characteristics, Challenges and Prospects (I) [J]. Petroleum Exploration and Development, 2015, 42(6): 689-701). Whereas, the lower flowback rate does not mean that it is not conducive to later production (Wang. Is Formation Damage an Issue in Shale Gas Development? SPE149263, 2012). Researchers and field engineers found that (Vandecasteele, I., et al., Impact of Shale Gas Development on Water Resources: A Case Study in Northern Poland. Environmental Management, 2015. 55(6): p. 1285-1299.), after completing the fracturing & stimulation, when the production well is opened again after a period of shut-in, the initial gas yield is higher than the production when the well is not shut in, and the water yield is reduced.

However, there are few studies on the testing device for the flowback rate of the shale gas well after fracturing at present. For example, the device invention (CN109490507A) of Chen Chi does not take into account the condition of the complex fracture network in the shale SRV fracturing. In the invention (CN106596380A) of Li Wuguang, a fracture network may be formed but only the confining pressure and the temperature are loaded for the rock core, which is different from the actual conditions of the reservoir under the horizontal principal stress and the vertical stress, Therefore, it is necessary to study the device and method for testing the flowback in the shut-in period of the shale gas well under real formation conditions to effectively evaluate and guide the flowback operation in the shut-in well of the shale reservoir.

SUMMARY OF THE INVENTION

The present invention mainly proposes a testing device and method for simulating the flowback in the shut-in period of fractured wells to overcome the shortcomings in the prior art. The present invention considers the in-situ stress and the temperature so as to be more close to actual conditions to simulate the law of well shut-in and flowback. The present invention also considers the flowback capacity under the condition of complex fracture network caused by the shale volume stimulation, and a passive acoustic wave monitoring system enables the evaluation of the fracturing fluid flowback capacity under different degrees of fracture network complexity.

The technical solution provided by the present invention to solve the above technical problems is: a testing device for simulating the flowback in the shut-in period of fractured wells, comprising a fracturing fluid tank, a flowback fracturing fluid tank, a hydraulic fracturing pump, a flowback fluid collection beaker, and a shut-in flowback testing system;

The shut-in flowback testing system is composed of a box body and an acoustic wave testing device, a temperature control device, a fracturing string and a square rock block arranged in the box body;

A stress loading plate and a hydraulic block are successively arranged between the four surfaces of the square rock block and the inner walls of the box body;

The acoustic wave testing device consists of an acoustic wave transmitting probe and an acoustic wave receiving probe, the acoustic wave transmitting probe is embedded in one stress loading plate, and the acoustic wave receiving probe is embedded in the other two stress loading plates;

The four outer surfaces of the box body are provided with hydraulic tanks, and the hydraulic tank contains hydraulic fluid which can be injected into the hydraulic block;

A hole is made on the fracturing string, one end of which is located in the square rock block and the other end is connected to the outlet of the hydraulic fracturing pump with a fracturing pipe; the fracturing pipe is provided with a flowback fracturing fluid pipe connected to the flowback fracturing fluid tank and a flowback pipe connected to the flowback fluid collection beaker;

The fracturing fluid tank is connected to the inlet of the hydraulic fracturing pump with a pipe; a valve I is provided between the hydraulic fracturing pump and the fracturing fluid tank; the hydraulic fracturing pump is provided with a parallel pipe, and the parallel pipe is provided with a valve II;

The flowback pipe is provided with a flowback electromagnetic flowmeter and a valve III, the flowback fracturing fluid pipe is provided with a valve VI, and the fracturing pipe is provided with a fracturing electromagnetic flowmeter, a valve IV and a valve V;

An electronic balance I, an electronic balance II and an electronic balance III are provided below the fracturing fluid tank, the flowback fluid collection beaker, and the flowback fracturing fluid tank respectively.

A further technical solution is that the electronic balance I, the electronic balance II and the electronic balance III are all equipped with an electronic balance shield.

A further technical solution is that the flowback pressure gauge is provided on the parallel pipe and fracturing pressure gauge is provided on the fracturing pipe.

A further technical solution is that the device further comprises a data recording computer which is connected to the flowback pressure gauge, the fracturing pressure gauge, the electronic balance I, the electronic balance II, and the electronic balance III via data transmission cables.

A further technical solution is that the stress loading plate embedded in the acoustic wave transmitting probe is placed perpendicular to the surface of the square rock block which is used to simulate horizontal wellbore and the other two stress loading plates embedded in the acoustic wave receiving probe are respectively placed on the surface of the square rock block adjacent to the former.

A further technical solution is that the device further comprises an experimental condition control computer which is respectively connected with the acoustic wave transmitting probe and the acoustic wave receiving probe via data transmission cables.

A test method for simulating the flowback in the shut-in period of fractured wells, comprising the following steps:

(1) According to the experimental requirements, prepare the required fracturing fluid, polish the rock sample to be a cube with a size of 70 cm×70 cm×70 cm, drill a channel with the same outer diameter and length as the fracturing string in the direction of the maximum horizontal principal stress, and put the rock block into the shut-in flowback testing system;

(2) Before the fracturing operation, the shut-in flowback testing system is not connected to the pipe temporarily; firstly turn on the experimental condition control computer, inject the fracturing fluid into the hydraulic block 106 through the hydraulic tank 104, that is, load the horizontal principal stress and the vertical stress, then turn on the temperature control device to reach the temperature of the simulated formation, turn on the acoustic wave testing device, and measure the initial acoustic wave data of the rock block;

(3) Before the fracturing operation, first test the amount of the residual fracturing fluid in the fracturing pipe and the flowback pipe with water, comprising the following steps: Record the data $M_1$ after the electronic balance I is stable, open the valve I, valve IV and valve V related to the fracturing operation, close the valve II, valve III and valve VI of the flowback pipe, turn on the hydraulic fracturing pump and set the displacement, and record the data $M_2$ of the electronic balance I when the pipe nozzle connecting the fracturing string begins to flow water; the difference between $M_1$ and $M_2$ is the amount of residual fracturing fluid in the pipe during the fracturing operation;

Drain the fluid in the tested pipe, close the valve I, valve IV and valve VI related to the fracturing operation, read the reading $M_3$ of the electronic balance III of the fracturing fluid tank, open the valve II, valve IV and valve VI of the flowback pipe, turn on the hydraulic fracturing pump and set the displacement, and record the data $M_4$ of the electronic balance III when the pipe nozzle at the flowback fluid collection beaker begins to flow water; the difference between $M_3$ and $M_4$ is the amount of residual fracturing fluid in the pipe during the flowback;

(4) Drain the residual fluid in the pipe, connect the shut-in flowback testing system to the pipe nozzle, and load the prepared fracturing fluid into the fracturing fluid tank; after the reading is stable, read the mass $M_5$ of the fracturing fluid tank, open the valve I, valve IV and valve V related to the fracturing operation, close the valve II, valve III and valve VI of the flowback pipe, and turn on the acoustic wave testing device and the computer connected to such device;

(5) Turn on the hydraulic fracturing pump, perform the fracturing operation according to the experimentally designed displacement, and then use the computer to process the data transmitted by the acoustic wave probe to obtain the real-time three-dimensional morphology of the fracturing network during this process; since there are only three surfaces equipped with acoustic wave testing devices, the fracture morphology interpreted by the testing device is half of the actual fracture morphology;

(6) After the fracture network meets the requirements of the experimental test, record the pressure $P_1$ and the data $M_6$ of the electronic balance I of the fracturing fluid tank at the same time, close the fracturing valve to simulate the fracturing fluid in the shut-in well under $P_1$ pressure, and record the fracture network morphology at this time;

(7) After the shut-in time reaches the experimental requirements, open the relevant valve II, valve III and valve VI of the flowback pipe, and close the valve I, valve IV and valve V related to the fracturing operation, turn on the hydraulic fracturing pump to perform the flowback operation under the experimentally designed pressure difference $\Delta P_2$, and at the same time, the electronic balance II starts to record the mass of flowback fluid in real time until the value $M_7$ is stable;

(8) Calculation of flowback rate:

Residual amount in fracturing pipe:

$$V_{R-HF} = \frac{M_1 - M_2}{\rho_{Water}}$$

Residual amount in flowback pipe:

$$V_{R-FL} = \frac{M_3 - M_4}{\rho_{Water}}$$

Amount of fracturing fluid injected into wellbore:

$$V_{HF} = \frac{M_5 - M_6}{\rho_f} - V_{R-HF}$$

Total amount of flowback fluid:

$$V_{FL} = \frac{M_7}{\rho_f} + V_{R-FL}$$

Then the flowback rate is:

$$\eta = \frac{V_{FL}}{V_{HF}}$$

(9) When testing and comparing the flowback rate of the rock block under different degrees of fracture network complexity, portray the fracture network formed in the rock block according to the data from the acoustic wave receiving probe, and quantify the complexity of the fracture network according to the concept of fracture network volume, namely:

$$FC = \sum_{i=1}^{n} L_i \times W_i \times H_i$$

In the formula: $M_1$ is the initial mass of the fracturing fluid tank when the residual amount in the fracturing pipe is tested with water, in g; $M_2$ is the mass of the fracturing fluid tank after the entire pipe is filled with water when the residual amount in the fracturing pipe is tested by water, in g; $M_3$ is the initial mass of the flowback fluid tank when the residual amount in the flowback pipe is tested with water, in g; $M_4$ is the mass of the flowback fluid tank after the entire pipe is filled with water when the residual amount in the fracturing pipe is tested by water, in g; $M_5$ is the initial mass of the fracturing fluid tank during fracturing operation, in g; $M_6$ is the mass of the fracturing fluid tank when the fracturing operation is completed, in g; $M_7$ is the mass of the flowback fluid collected in the beaker after the completion of the flowback operation, in g; $\rho_{water}$ is the density of the water used to test the residual amount in the pipe, in g/cm$^3$; $\rho_f$ is the density of fracturing fluid designed in the experiment, in g/cm$^3$; $\eta$ is the flowback rate, dimensionless; FC is the fracture network volume of the rock block, in cm$^3$; $L_i$ is the length of the $i^{th}$ cluster fracture in the fracture network portrayed by the computer, in cm; W is the width of the $i^{th}$ cluster fracture in the fracture network portrayed by the computer, in cm; H is the height of the $i^{th}$ cluster fracture in the fracture network portrayed by the computer, in cm.

(10) Finally, obtain the relationship between the fracture network volume and the flowback rate.

The advantages of the present invention are: compared with the prior art, the present invention considers the in-situ stress of the rock block, such as the horizontal principal stress and the vertical stress, and also considers the influence of the formation temperature, so as to be closer to actual conditions of the formation. In addition, since the residual fracturing fluid in the pipe of the device has a greater influence on the test result of the flowback capacity, the present invention takes into account the influence of the residual amount in the pipe, and can more accurately quantify the flowback capacity of the retained fracturing fluid after the well is shut in. The present invention adopts the passive acoustic wave testing technology to monitor the fracture network in real time and compare the flowback capacity of the fracture network with different complexity.

DETAILED DESCRIPTION OF THE PREFERRED EMBODIMENTS

The present invention will be further described with the following embodiments and figures.

Figure 2:
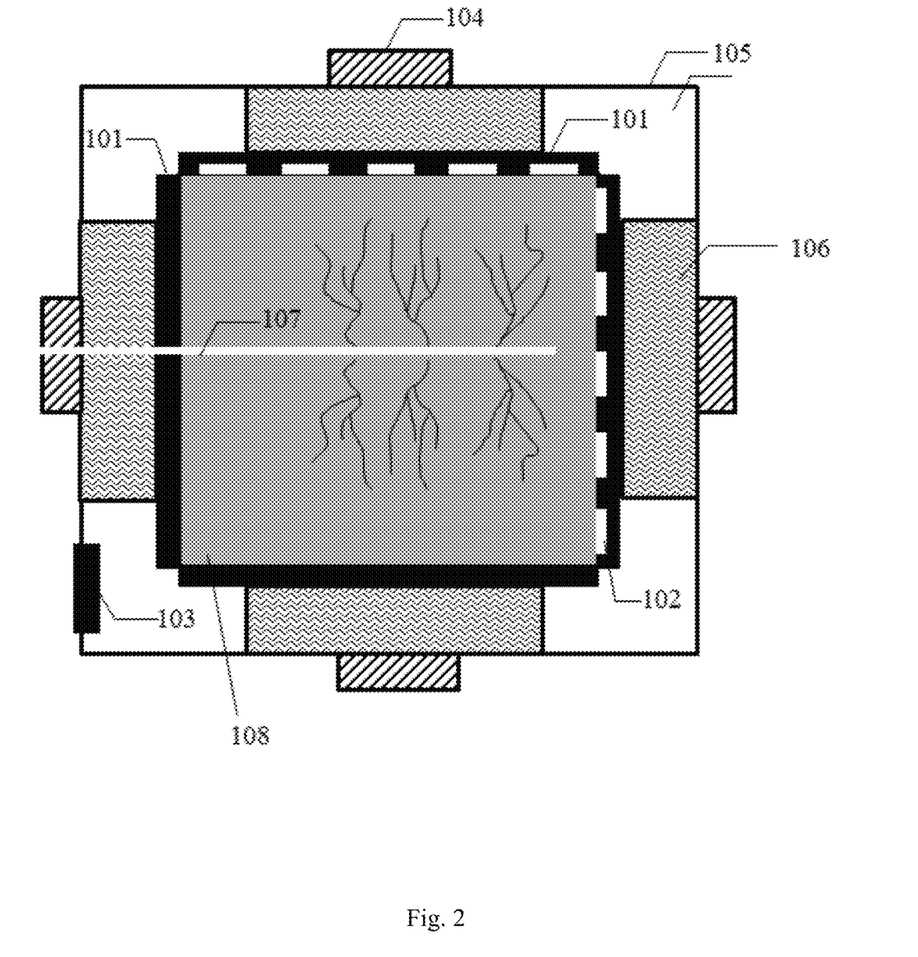
FIG. 2 is a structural diagram of shut-in flowback testing system.
Figure 5:
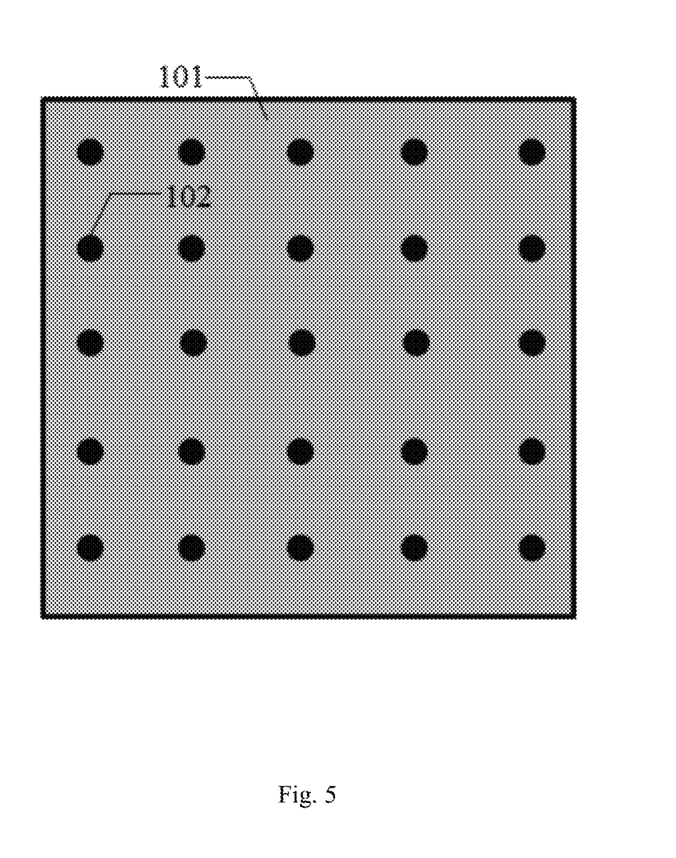
FIG. 5 is a structural diagram of stress loading plate embedded with acoustic wave probe.

As shown in FIGS. 1-5, a testing device for simulating the flowback in the shut-in period of fractured wells, comprising a fracturing fluid tank 2, a flowback fracturing fluid tank, a hydraulic fracturing pump 5, a flowback fluid collection beaker 9, and a shut-in flowback testing system 10;

The shut-in flowback testing system 10 is composed of a box body 105 and an acoustic wave testing device 102, a temperature control device 103, a fracturing string 107 and a square rock block 108 arranged in the box body 105;

A stress loading plate 101 and a hydraulic block 106 are successively arranged between the four surfaces of the square rock block 108 and the inner walls of the box body 105;

It can be ensured that the area of the stress loading plate 101 is greater than or equal to the single-sided area of the rock block. The acoustic wave testing device 102 consists of an acoustic wave transmitting probe and an acoustic wave receiving probe. Three stress loading plates 101 are embedded with 25 probes (as shown in FIG. 5). The three plates are arranged adjacent to each other, among which one is embedded with the acoustic wave transmitting probe and placed perpendicular to the surface of the rock block which is used to simulate the horizontal wellbore, and the other two are embedded with the acoustic wave receiving probe and respectively placed on the surface of the rock block adjacent to the former.

The acoustic wave testing device 102 can be wirelessly connected to the computer, and interpret the fracture network in the rock block through the changes of acoustic wave on the basis of the principle of the passive acoustic wave monitoring.

The four outer surfaces of the box body 105 are provided with hydraulic tanks 104, and the hydraulic tank 104 contains hydraulic fluid which can be injected into the hydraulic block 106; the hydraulic block 106 can exert stress on the square rock block through expansion, and the hydraulic block 106 will not deform in the process of applying stress.

Figure 3:
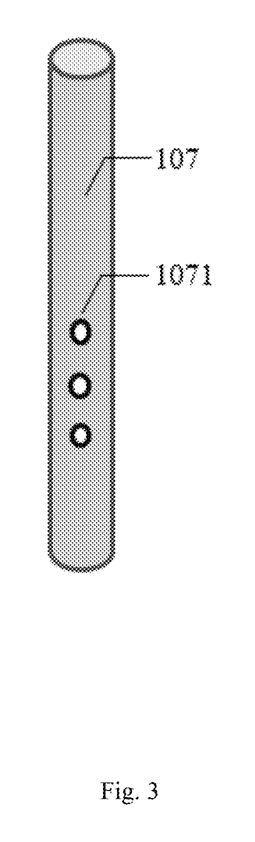
FIG. 3 is a structural diagram of fracturing string.
Figure 4:
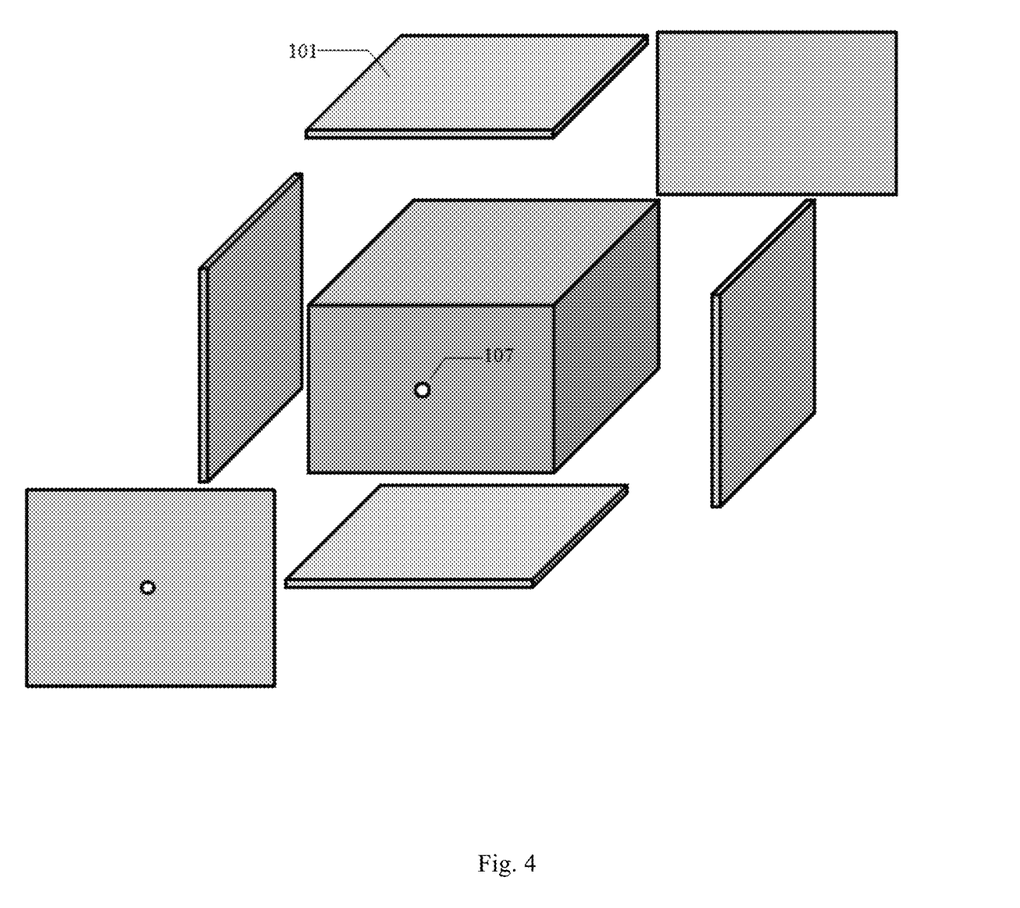
FIG. 4 is an overall view of rock block and stress loading plate.

A hole 1071 is made on the fracturing string 107. In the experiment, the hole spacing and arrangement are selected according to the needs, but not limited to the figures attached in the present invention.

Figure 1:
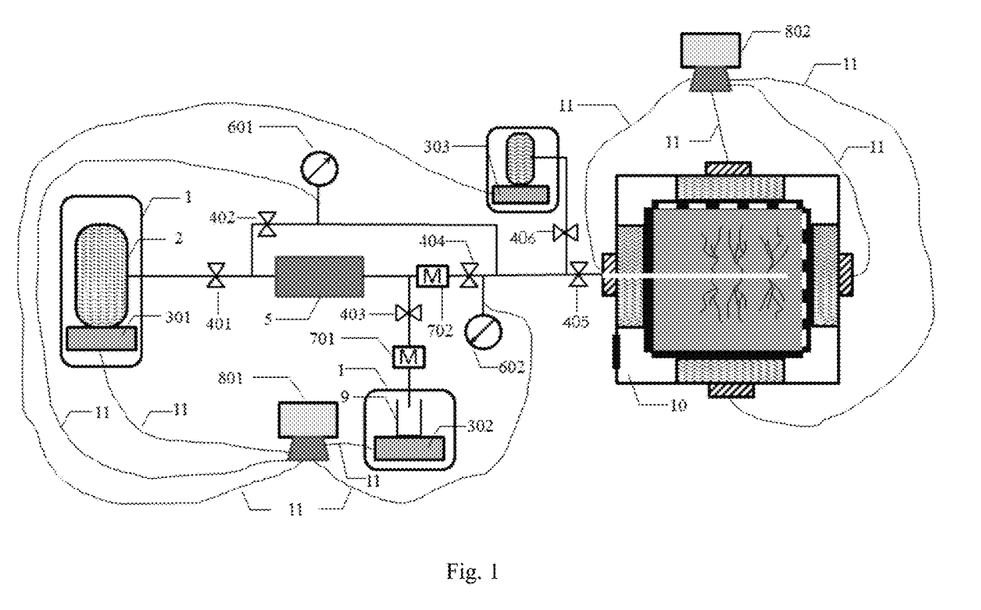
FIG. 1 is a structural diagram of the experimental device of the present invention.

One end of the fracturing string 107 is arranged in the square rock block 108 after passing through the hydraulic tank 104, the box body 105, the hydraulic block 106 and the stress loading plate 101, the other end is connected to the outlet of the hydraulic fracturing pump 5 with a fracturing pipe; the fracturing pipe is provided with a flowback fracturing fluid pipe connected to the flowback fracturing fluid tank and a flowback pipe connected to the flowback fluid collection beaker 9;

The fracturing fluid tank 2 is connected to the inlet of the hydraulic fracturing pump 5 with a pipe; a valve I 401 is provided between the hydraulic fracturing pump 5 and the fracturing fluid tank 2; the hydraulic fracturing pump 5 is provided with a parallel pipe, and the parallel pipe is provided with a valve II 402;

A flowback pressure gauge 601 is provided on the parallel pipe and a fracturing pressure gauge 602 is provided on the fracturing pipe;

The flowback pipe is provided with a flowback electromagnetic flowmeter 701 and a valve III 403, the flowback fracturing fluid pipe is provided with a valve VI 406, and the fracturing pipe is provided with a fracturing electromagnetic flowmeter 702, a valve IV 404 and a valve V 405;

An electronic balance I 301, an electronic balance II 302 and an electronic balance III 303 are provided below the fracturing fluid tank 2, the flowback fluid collection beaker 9, and the flowback fracturing fluid tank respectively.

In this embodiment, as shown in FIG. 1, the electronic balance I 301, the electronic balance II 302 and the electronic balance III 303 are all equipped with an electronic balance shield 1, that is, the fracturing fluid tank 2, the flowback fracturing fluid tank and the flowback fluid collection beaker 9 are all located in the electronic balance with an electronic balance shield 1 which is used to eliminate the influence of external air flow and other factors on the data measured by the balance to ensure the accuracy of the data. The accuracy of the electronic balance is 0.00001 g. The data transmission cable 11 can transmit the reading of the measuring device to the computer in real time.

In this embodiment, as shown in FIG. 1, in order to obtain accurate data quickly, the preferred embodiment is that the device also includes a data recording computer 801, and the data recording computer 801 is connected to the flowback pressure gauge 601, the fracturing pressure gauge 602, the electronic balance I 301, the electronic balance II 302, and the electronic balance III 303 via data transmission cables 11.

The device further comprises an experimental condition control computer 802 which is respectively connected with the acoustic wave transmitting probe and the acoustic wave receiving probe via data transmission cables 11.

Figure 6:
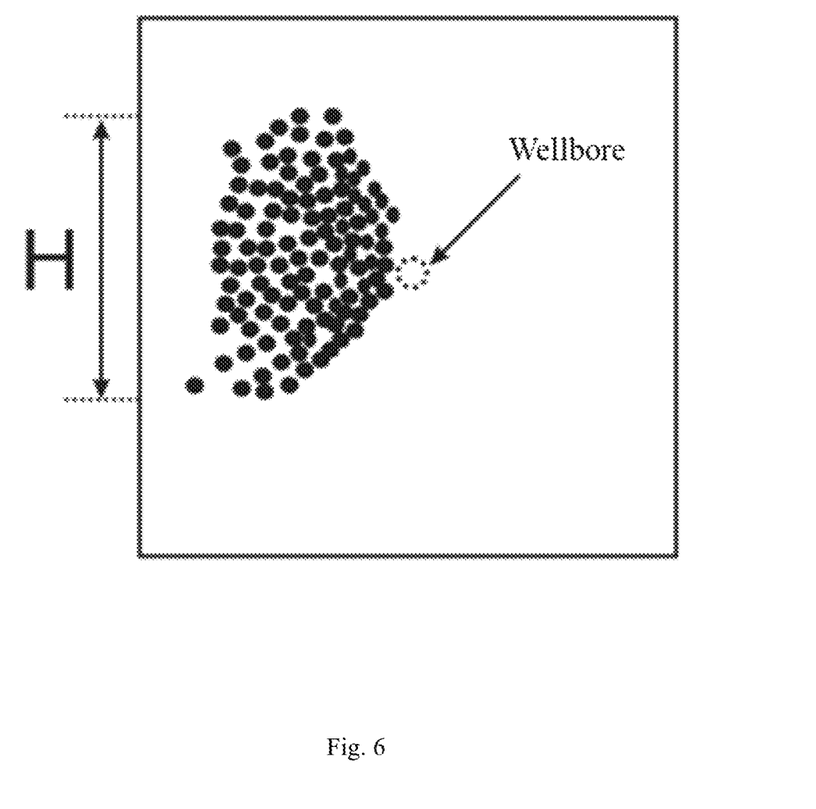
FIG. 6 is a side view of fracture network of rock block portrayed according to the acoustic wave data.
Figure 7:
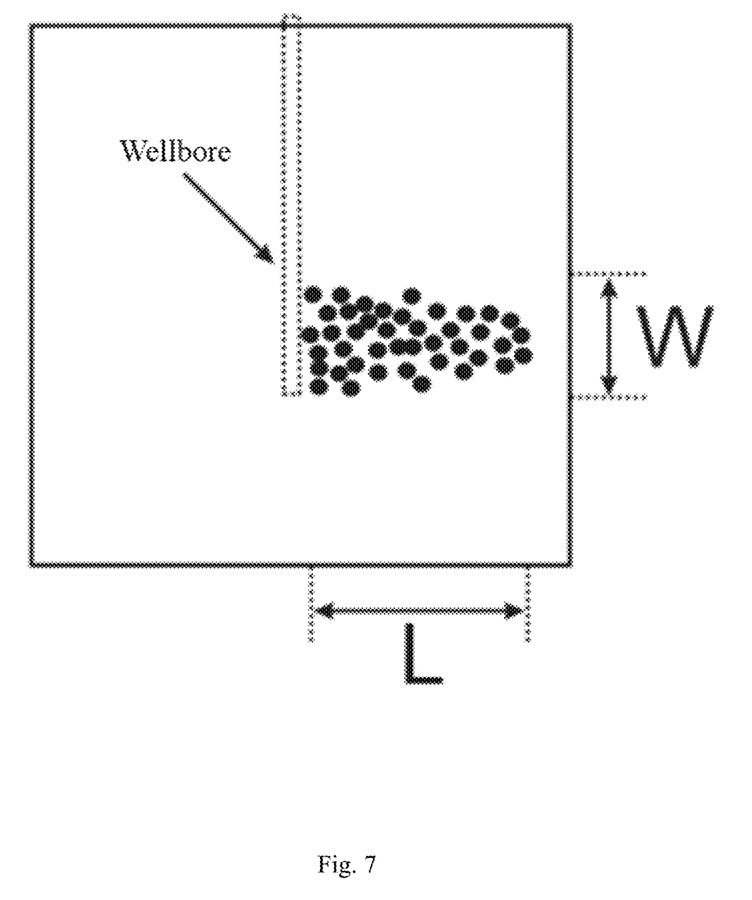
FIG. 7 is a top view of fracture network of rock block portrayed according to the acoustic wave data.

A test method for simulating the flowback in the shut-in period of fractured wells, comprising the following steps:
(1) According to the experimental requirements, prepare the required fracturing fluid, polish the rock sample to be a cube with a size of 70 cm×70 cm×70 cm, drill a channel with the same outer diameter and length as the fracturing string 107 in the direction of the maximum horizontal principal stress, and put the rock block into the shut-in flowback testing system;
(2) Before the fracturing operation, the shut-in flowback testing system is not connected to the pipe temporarily; firstly turn on the experimental condition control computer 802, inject the fracturing fluid into the hydraulic block 106 through the hydraulic tank 104, that is, load horizontal principal stress and vertical stress, then turn on the temperature control device 103 to reach the temperature of the simulated formation, turn on the acoustic wave testing device 102, and measure the initial acoustic wave data of the rock block;
(3) Before the fracturing operation, first test the amount of residual fracturing fluid in the fracturing pipe and the flowback pipe with water, comprising the following steps: Record the data $M_1$ after the electronic balance I 301 is stable, open the valve I 401, valve IV 404 and valve V 405 related to the fracturing operation, close the valve II 402, valve III 403 and valve VI 406 of the flowback pipe, turn on the hydraulic fracturing pump 5 and set the displacement, and record the data $M_2$ of the electronic balance I 301 when the pipe nozzle connecting the fracturing string begins to flow water; the difference between $M_1$ and $M_2$ is the amount of residual fracturing fluid in the pipe during the fracturing operation;

Drain the fluid in the tested pipe, close the valve I 401, valve IV 404 and valve VI 406 related to the fracturing operation, read the reading $M_3$ of the electronic balance III 303 of the fracturing fluid tank, open the valve II 402, valve IV 404 and valve VI 406 of the flowback pipe, turn on the hydraulic fracturing pump 5 and set the displacement, and record the data $M_4$ of the electronic balance III 303 when the pipe nozzle at the flowback fluid collection beaker 9 begins to flow water; the difference between $M_3$ and $M_4$ is the amount of residual fracturing fluid in the pipe during the flowback;

(4) Drain the residual fluid in the pipe, connect the shut-in flowback testing system to the pipe nozzle, and load the prepared fracturing fluid into the fracturing fluid tank 2; after the reading is stable, read the mass $M_5$ of the fracturing fluid tank 2, open the valve I 401, valve IV 404 and valve V 405 related to the fracturing operation, close the valve II 402, valve III 403 and valve VI 406 of the flowback pipe, and turn on the acoustic wave testing device 102 and the computer connected to such device;

(5) Turn on the hydraulic fracturing pump 5, perform the fracturing operation according to the experimentally designed displacement, and then use the computer to process the data transmitted by the acoustic wave probe to obtain the real-time three-dimensional morphology of the fracturing network during this process, as shown in FIG. 6 and FIG. 7; since there are only three surfaces equipped with the acoustic wave testing devices 102, the fracture morphology interpreted by the testing device is half of the actual fracture morphology;

(6) After the fracture network meets the requirements of the experimental test, record the pressure $P_1$ and the data $M_6$ of the electronic balance I 301 of the fracturing fluid tank 2 at the same time, close the fracturing valve to simulate the fracturing fluid in the shut-in well under $P_1$ pressure, and record the fracture network morphology at this time;

(7) After the shut-in time reaches the experimental requirements, open the relevant valve II 402, valve III 403 and valve VI 406 of the flowback pipe, and close the valve I 401, valve IV 404 and valve V 405 related to the fracturing operation, turn on the hydraulic fracturing pump 5 to perform the flowback operation under the experimentally designed pressure difference $\Delta P_2$, and at the same time, the electronic balance II 302 starts to record the mass of flowback fluid in real time until the value $M_7$ is stable;

(8) Calculate the flowback rate;

Residual amount in fracturing pipe:

$$V_{R-HF} = \frac{M_1 - M_2}{\rho_{Water}}$$

Residual amount in flowback pipe:

$$V_{R-FL} = \frac{M_3 - M_4}{\rho_{Water}}$$

Amount of fracturing fluid injected into wellbore:

$$V_{HF} = \frac{M_5 - M_6}{\rho_f} - V_{R-HF}$$

Total amount of flowback fluid:

$$V_{FL} = \frac{M_7}{\rho_f} + V_{R-FL}$$

Then the flowback rate is:

$$\eta = \frac{V_{FL}}{V_{HF}}$$

(9) When testing and comparing the flowback rate of the rock block under different degrees of fracture network complexity, portray the fracture network formed in the rock block according to the data from the acoustic wave receiving probe, and quantify the complexity of the fracture network according to the concept of fracture network volume, namely:

$$FC = \sum_{i=1}^{n} L_i \times W_i \times H_i$$

Figure 8:
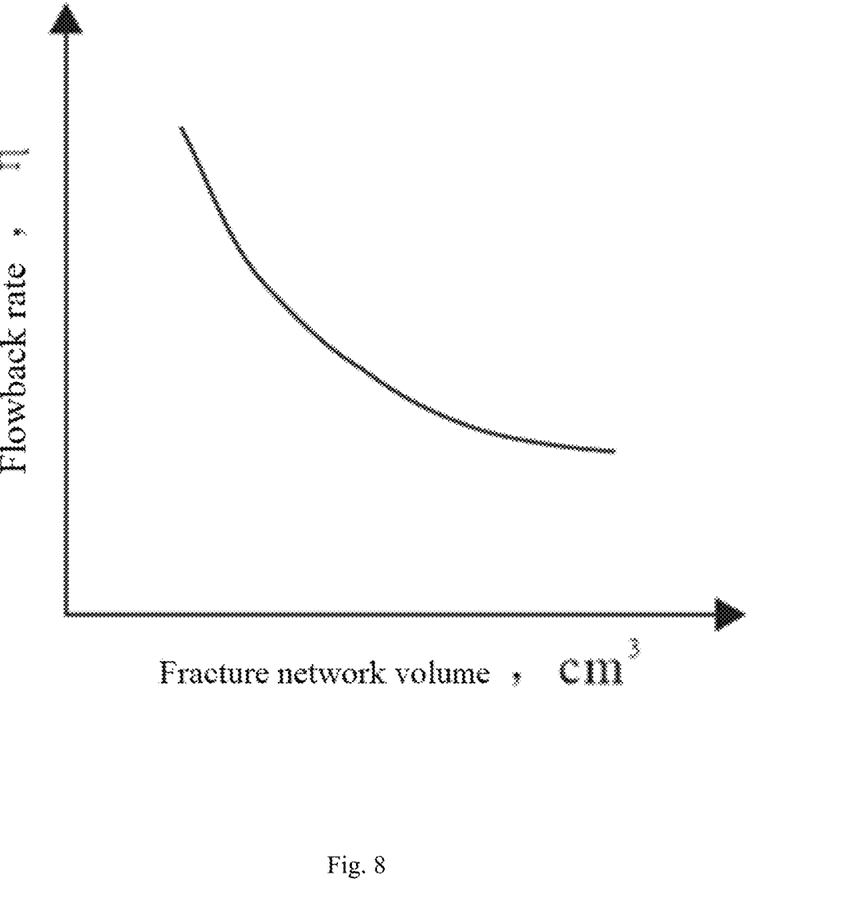
FIG. 8 is a chart of the relationship between fracture network volume and flowback capacity.

(10) Finally, obtain the relationship between the fracture network volume and the flowback rate, as shown in FIG. 8

The above are not intended to limit the present invention in any form. Although the present invention has been disclosed as above with embodiments, it is not intended to limit the present invention. Those skilled in the art, within the scope of the technical solution of the present invention, can use the disclosed technical content to make a few changes or modify the equivalent embodiment with equivalent changes. Within the scope of the technical solution of the present invention, any simple modification, equivalent change and modification made to the above embodiments according to the technical essence of the present invention are still regarded as a part of the technical solution of the present invention.

The invention claimed is:

1. A testing system for simulating flowback in a shut-in period of fractured wells, the testing system comprising:
    a fracturing fluid tank, a flowback fracturing fluid tank, a hydraulic fracturing pump, a flowback fluid collection beaker, and a shut-in flowback testing system;
    wherein the shut-in flowback testing system comprises a box body, an acoustic wave testing device, a temperature control device, a fracturing string and a cube rock block arranged in the box body;
    wherein four stress loading plates and four hydraulic blocks are successively and respectively arranged between four surfaces of the cube rock block and four inner walls of the box body; the acoustic wave testing device comprises an acoustic wave transmitting probe and two acoustic wave receiving probes, the acoustic wave transmitting probe being embedded in a first stress loading plate among the four stress loading plates, and the two acoustic wave receiving probes being respectively embedded in a second stress loading plate and a third stress loading plate among the four stress loading plates that are adjacent to the first stress loading plate; four outer surfaces of the box body are provided with four hydraulic tanks, and each of the hydraulic tanks contains hydraulic fluid which is injected into the corresponding hydraulic block;
    wherein a hole is made on the fracturing string, a first end of the fracturing string is located in the cube rock block and a second end of the fracturing string is connected to an outlet of the hydraulic fracturing-pump with a fracturing pipe; the fracturing pipe is provided with a flowback fracturing fluid pipe connected to the flowback fracturing fluid tank and a flowback pipe connected to the flowback fluid collection beaker; the fracturing fluid tank is connected to an inlet of the hydraulic fracturing pump with a pipe;
    wherein a first valve is provided between the hydraulic fracturing pump and fracturing fluid tank; the hydraulic fracturing pump is provided with a parallel pipe, and the parallel pipe is provided with a second valve; the flowback pipe is provided with a flowback electromagnetic flowmeter and a third valve, the flowback fracturing fluid pipe is provided with a sixth valve, and the fracturing pipe is provided with a fracturing electromagnetic flowmeter, a fourth valve and a fifth valve; and a first electronic balance, a second electronic balance and a third electronic balance are disposed below the fracturing fluid tank, the flowback fluid collection beaker, and the flowback fracturing fluid tank respectively.

2. A test method for simulating flowback in a shut-in period of fractured wells, applied in the testing system according to claim 1, the method comprising the following steps:
    (1) preparing a fracturing fluid; polishing a rock sample to be the cube rock block with a size of 70 cm×70 cm×70 cm; drilling a channel with an identical outer diameter and an identical length as the fracturing string along a direction of a maximum horizontal principal stress; and putting the cube rock block into the shut-in flowback testing system;
    (2) disconnecting the shut-in flowback testing system from the pipe; turning on an experimental condition control computer; injecting the fracturing fluid into the four hydraulic blocks through the four hydraulic tanks; turning on the temperature control device to reach a simulated formation temperature; and turning on the acoustic wave testing device to measure an initial acoustic wave data of the cube rock block;
    (3) testing an amount of residual fracturing fluid in the fracturing pipe and an amount of residual fracturing fluid in the flowback pipe, comprising the following sub-steps:
        (3-A) recording a data $M_1$ after the first electronic balance is stable; opening the first valve, the fourth valve and the fifth valve on the fracturing pipe, and closing the second valve, the third valve and the sixth valve on the flowback pipe; turning on the hydraulic fracturing pump, and recording a data $M_2$ of the first electronic balance when a pipe nozzle connecting the fracturing string begins to flow water; wherein a difference between the data $M_1$ and the data $M_2$ is the amount of residual fracturing fluid in the fracturing pipe; and
        (3-B) draining the fracturing fluid in the pipe; closing the first valve, the fourth valve and the sixth valve on the fracturing pipe; reading a data $M_3$ of the third electronic balance of the fracturing fluid tank; opening the second valve, the fourth valve and the sixth valve on the flowback pipe; turning on the hydraulic fracturing pump and setting the displacement, and recording a data $M_4$ of the third electronic balance when a pipe nozzle at the flowback fluid collection beaker begins to flow water; wherein a difference between the data $M_3$ and the data $M_4$ is the amount of residual fracturing fluid in the flowback pipe;

(4) draining the residual fluid in the pipe; connecting the shut-in flowback testing system to the pipe, and loading the fracturing fluid into the fracturing fluid tank; reading a mass data $M_5$ of the fracturing fluid tank; opening the first valve, the fourth valve and the fifth valve on the fracturing pipe, and closing the second valve, the third valve and the sixth valve on the flowback pipe; and turning on the acoustic wave testing device and connecting the computer to the acoustic wave testing device;

(5) turning on the hydraulic fracturing pump; performing a fracturing operation, and using the computer to process a data transmitted by the acoustic wave probe to obtain a morphology of a fracturing network;

(6) recording a pressure $P_1$ and a mass data $M_6$ of the first electronic balance of the fracturing fluid tank, closing the fracturing valve to simulate the fracturing fluid in the shut-in well under the pressure $P_1$, and recording the morphology of the fracturing network;

(7) opening the second valve, the third valve and the sixth valve on the flowback pipe, and closing the first valve, the fourth valve and fifth valve on the fracturing pipe, turning on the hydraulic fracturing pump to perform a flowback operation under an experimentally designed pressure difference $\Delta P_2$; the second electronic balance recording a mass of flowback fluid in real time until a data $M_7$ is stable;

(8) calculating a flowback rate of the cube rock block;

(9) comparing the flowback rate of the cube rock block under different degrees of fracture network complexity, portraying the fracture network formed in the cube rock block according to the data from the acoustic wave receiving probe, and quantifying a complexity of the fracture network according to a fracture network volume; and (10) obtaining a relationship between the fracture network volume and the flowback rate.

* * * * *